(12) United States Patent
Isaac et al.

(10) Patent No.: US 12,157,123 B2
(45) Date of Patent: Dec. 3, 2024

(54) DEVICE AND METHOD FOR MICRODROPLET DETECTION OF CELLS

(71) Applicant: LIGHTCAST DISCOVERY LTD, Cambridge (GB)

(72) Inventors: Tom Isaac, Cambridge (GB); Cameron Frayling, Cambridge (GB)

(73) Assignee: LIGHTCAST DISCOVERY LTD, Cambridge (GB)

( * ) Notice: Subject to any disclaimer, the term of this patent is extended or adjusted under 35 U.S.C. 154(b) by 710 days.

(21) Appl. No.: 17/295,654

(22) PCT Filed: Nov. 8, 2019

(86) PCT No.: PCT/GB2019/053168
§ 371 (c)(1),
(2) Date: May 20, 2021

(87) PCT Pub. No.: WO2020/104769
PCT Pub. Date: May 28, 2020

(65) Prior Publication Data
US 2022/0008927 A1   Jan. 13, 2022

(30) Foreign Application Priority Data

Nov. 20, 2018 (EP) ..................... 18207377
Nov. 20, 2018 (EP) ..................... 18207379
Jul. 2, 2019 (GB) ..................... 1909514

(51) Int. Cl.
*B01L 1/00* (2006.01)
*B01L 3/00* (2006.01)
(Continued)

(52) U.S. Cl.
CPC ... *B01L 3/502761* (2013.01); *B01L 3/502715* (2013.01); *B01L 3/502784* (2013.01);
(Continued)

(58) Field of Classification Search
None
See application file for complete search history.

(56) References Cited

U.S. PATENT DOCUMENTS

| 6,565,727 | B1 | 5/2003 | Shenderov |
| 10,940,477 | B2 * | 3/2021 | Yu ..................... B01L 3/502761 |
| 2003/0224528 | A1 | 12/2003 | Chiou et al. |
| 2008/0053205 | A1 | 3/2008 | Pollack et al. |
| 2009/0155902 | A1 | 6/2009 | Pollack et al. |
| 2009/0203063 | A1 | 8/2009 | Wheeler et al. |
| 2011/0147215 | A1 | 6/2011 | Fuchs et al. |
| 2011/0186433 | A1 † | 8/2011 | Pollack |

(Continued)

FOREIGN PATENT DOCUMENTS

JP   2017-519620   7/2017
WO   2016/174523   11/2016
(Continued)

OTHER PUBLICATIONS

International Search Report issued Jan. 30, 2020 in corresponding PCT Application No. PCT/GB2019/053168.
(Continued)

*Primary Examiner* — Jyoti Nagpaul
(74) *Attorney, Agent, or Firm* — Porter Wright Morris & Arthur LLP

(57) ABSTRACT

Devices, systems, and associated methods are provided for manipulating and/or determining one or more characteristics of cells contained within a biological sample. In particular a device and methods of use thereof are provided, the device comprising a sorting component configured to separate cell-containing microdroplets from empty ones into a population of cell-containing first microdroplets; a microdroplet manipulation component configured to manipulate the first microdroplets using real or virtual electrowetting electrodes, and an optical detection system configured to detect an optical signal from the microdroplets via the one or more detection windows.

32 Claims, 2 Drawing Sheets

Figure 1:
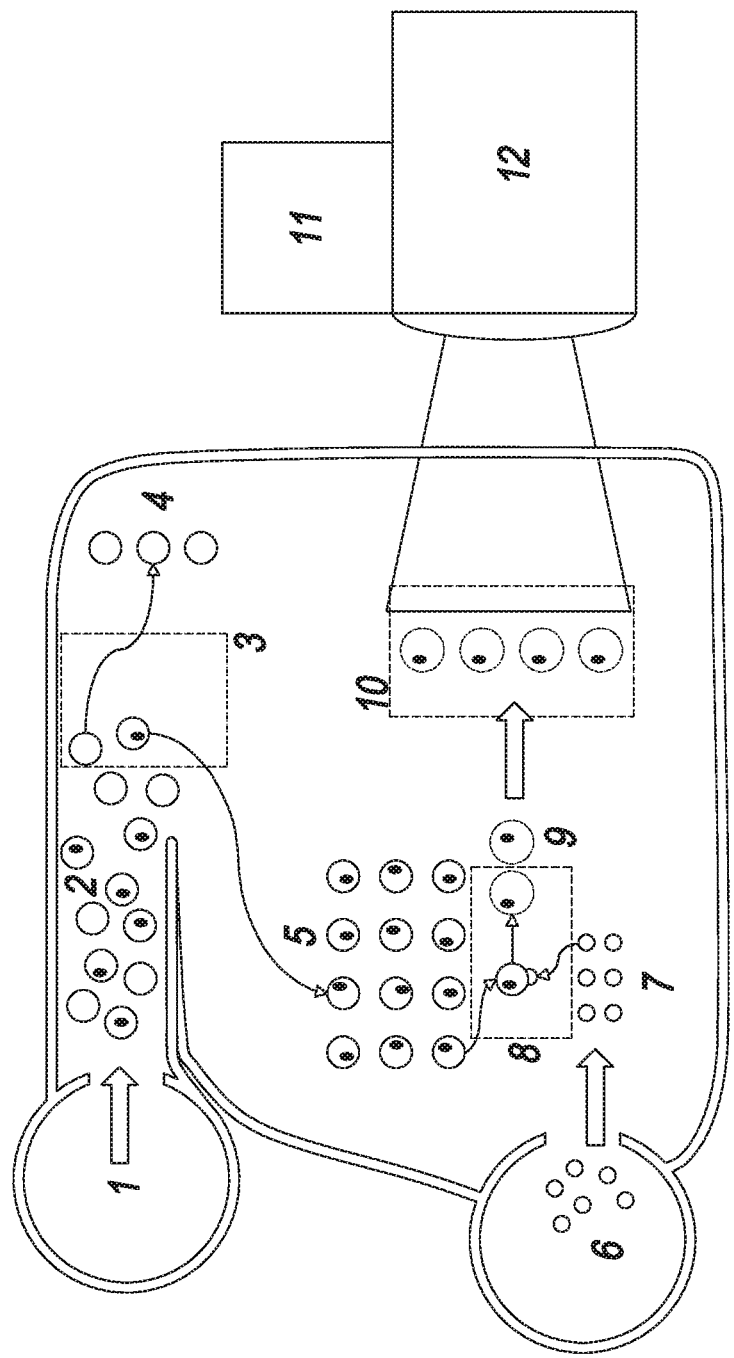

(51) Int. Cl.
  *C12N 5/0797* (2010.01)
  *C12N 13/00* (2006.01)
  *G01N 15/14* (2006.01)
  *G01N 15/1492* (2024.01)
  *G01N 33/58* (2006.01)
  *G01N 15/01* (2024.01)

(52) U.S. Cl.
  CPC ........... *C12N 5/0623* (2013.01); *C12N 13/00* (2013.01); *G01N 15/1484* (2013.01); *G01N 15/1492* (2024.01); *G01N 33/582* (2013.01); *B01L 2200/0652* (2013.01); *B01L 2200/0673* (2013.01); *B01L 2300/0645* (2013.01); *B01L 2300/0663* (2013.01); *B01L 2300/0864* (2013.01); *B01L 2300/10* (2013.01); *B01L 2400/0427* (2013.01); *G01N 15/01* (2024.01); *G01N 2015/1481* (2013.01)

(56) References Cited

U.S. PATENT DOCUMENTS

| | | | |
|---|---|---|---|
| 2013/0143312 A1† | 6/2013 | Wheeler | |
| 2013/0233425 A1 | 9/2013 | Srinivasan et al. | |
| 2014/0124037 A1 | 5/2014 | Foley | |
| 2014/0262783 A1† | 9/2014 | Chang | |
| 2015/0027889 A1 | 1/2015 | Pollack et al. | |
| 2015/0298125 A1 | 10/2015 | Ermakov | |
| 2016/0102280 A1 | 4/2016 | Tovar et al. | |
| 2016/0158748 A1 | 6/2016 | Wu et al. | |
| 2016/0160259 A1 | 6/2016 | Du | |
| 2017/0121675 A1 | 5/2017 | Sugarman | |
| 2018/0133715 A1 | 5/2018 | Craig et al. | |
| 2018/0313819 A1 | 11/2018 | Pugia et al. | |
| 2018/0334670 A1 | 11/2018 | Bharadwaj et al. | |

FOREIGN PATENT DOCUMENTS

| | | | |
|---|---|---|---|
| WO | 2016174523 A1 † | 11/2016 | |
| WO | 2016/193758 | 12/2016 | |
| WO | 2017/117567 | 7/2017 | |
| WO | 2018/234445 | 12/2018 | |
| WO | 2018/234448 | 12/2018 | |

OTHER PUBLICATIONS

Written Opinion of the International Searching Authority issued Jan. 30, 2020 in corresponding PCT Application No. PCT/GB2019/053168.
Partial European Search Report issued Apr. 23, 2019 in corresponding European Patent Application No. 18207379.1.
European Search Report issued Apr. 5, 2019 in corresponding European Patent Application No. 18207377.
Extended European Search Report issued Jul. 26, 2019 in corresponding European Patent Application No. 18207379.1.
Patents Act 1977: Search Report under Section 17(5) issued Jan. 31, 2020 in corresponding United Kingdom Application No. 1909514.0.
Jing et al., "Jetting microfluidics with size-sorting capability for single-cell protease detection", Biosensors and Bioelectronics, 2014, vol. 66, pp. 19-23.
Park et al., "On-chip characterization of cryoprotective agent mixtures using an EWOD-based digital microfluidic device", Lab On a Chip, 2011, vol. 11, No. 13, pp. 2212-2221.
Huang et al., "Fertilization of Mouse Gametes in Vitro Using a Digital Microfluidic System", IEEE Transactions On Nanobioscience, 2015, vol. 14, No. 8, pp. 857-863.
Huang et al., "Digital Microfluidic Dynamic Culture of Mammalian Embryos on an Electrowetting on Dielectric (EWOD) Chip", PLOS ONE, 2015, vol. 10, No. 5, e0124196, 15 pages.
Chiou et al., "Pico Liter Droplet Manipulation Based On a Novel Continous Opto-Electrowetting Mechanism", 12th International Conference on Solid-State Sensors, Actuators and Microsystems, Transducers '03, 2003, vol. 1, pp. 468-471.
Ng et al., "Digital Microfluidic Cell Culture", Annual Review of Biomedical Engineering, 2015, vol. 17, No. 1, pp. 91-112.
Kalsi, S.; Sellars, S.L.; Turner, C.; Sutton, J.M.; Morgan, H. "A Programmable Digital Microfluidic Assay for the Simultaneous Detection of Multiple Anti-Microbial Resistance Genes" Micromachines 2017, 8, 111.†
George, Subin M., and Hyejin Moon. "Digital microfluidic three-dimensional cell culture and chemical screening platform using alginate hydrogels." Biomicrofluidics 9.2 (2015): 024116.†
Huang HY, Shen HH, Tien CH, Li CJ, Fan SK, et al. (2015) "Digital Microfluidic Dynamic Culture of Mammalian Embryos on an Electrowetting on Dielectric (EWOD) Chip" PLOS ONE 10(5): e0124196.†
Pei, Shao Ning, et al. "Light-actuated digital microfluidics for large-scale, parallel manipulation of arbitrarily size droplets." 2010 IEEE 23rd international conference on micro electro mechanical systems (MEMS). IEEE, 2010.†
Barbulovic-Nad, Irena, Sam H. Au, and Aaron R. Wheeler. "A microfluidic platform for complete mammalian cell culture." Lab on a Chip 10.12 (2010): 1536-1542.†
Gérard, A., Woolfe, A., Mottet, G. et al. "High-throughput single-cell activity-based screening and sequencing of antibodies using droplet microfluidics" Nature Biotechnology 38, 715-721 (2020).†

* cited by examiner
† cited by third party

DEVICE AND METHOD FOR MICRODROPLET DETECTION OF CELLS

According to the present invention a device and related methods are provided for the rapid identification, manipulation and selection of cells. It is especially useful for the manipulation of mammalian cells, either from immortalised cell culture samples or directly from tissue samples. It is also especially useful for the rapid and parallel screening of patient samples thought to contain evidence of infections.

Devices for manipulating droplets or magnetic beads have been previously described in the art; see for example U.S. Pat. No. 6,565,727, US20130233425 and US20150027889. In the case of droplets, this outcome may be typically achieved by causing the droplets, for example in the presence of an immiscible carrier fluid, to travel through a microfluidic space defined by two opposed walls of a cartridge or microfluidic tubing. Embedded within one or both of these walls are microelectrodes covered with a dielectric layer each of which is connected to an A/C biasing circuit capable of being switched on and off rapidly at intervals to modify the electric field characteristics of the layer. This gives rise to localised directional capillary forces in the vicinity of the microelectrodes which can be used to steer the droplet along one or more predetermined pathways. Such devices, which employ what hereinafter and in connection with the present invention will be referred to as 'real' electrowetting electrodes, are known in the art by the acronym EWOD (Electrowetting on Dielectric) devices.

A variant of this approach, in which the electrowetting forces are optically-mediated, known in the art as optoelectrowetting and hereinafter the corresponding acronym OEWOD, has been disclosed in, for example, US20030224528, US20150298125, US20160158748, US20160160259 and Applied Physics Letters 93 221110 (2008). In particular, the first of these three patent applications discloses various microfluidic devices which include a microfluidic cavity defined by first and second walls and wherein the first wall is of composite design and comprised of substrate, photoconductive and insulating (dielectric) layers. In this single-sided embodiment, between the photoconductive and insulating layers is disposed an array of conductive cells which are electrically isolated from one another and coupled to the photoactive layer and whose functions are to generate corresponding electrowetting electrode locations on the insulating layer. At these locations, the surface tension properties of the droplets can be modified by means of an electrowetting field as described above. The conductive cells may then be temporarily switched on by light impinging on the photoconductive layer. This approach has the advantage that switching is made much easier and quicker although its utility is to some extent still limited by the arrangement of the electrodes. Furthermore, there is a limitation as to the speed at which droplets can be moved and the extent to which the actual droplet pathway can be varied.

Double-sided embodiments of this latter approach have been disclosed in University of California at Berkeley thesis UCB/EECS-2015-119 by Pei. In one example, a cell is described which allows the manipulation of relatively large droplets in the size range 100-500 μm using optoelectrowetting across a surface of Teflon AF deposited over a dielectric layer using a light-pattern over electrically-biased amorphous silicon. However, in the devices exemplified the dielectric layer is thin (100 nm) and only disposed on the wall bearing the photoactive layer.

In our published application WO 2018/234445, the entirety of which is incorporated by reference herein, we have described a device for manipulating microdroplets which uses optoelectrowetting to provide the motive force. In this optically mediated electrowetting (OEWOD) device, the microdroplets are translocated through a microfluidic space defined by containing walls; for example a pair of parallel plates having the microfluidic space sandwiched therebetween. At least one of the containing walls includes what are hereinafter referred to as 'virtual' electrowetting electrodes locations which are generated by selectively illuminating an area of a semiconductor layer buried within. By selective illumination of the layer with light from a separate light source, a virtual pathway of virtual electrowetting electrode locations can be generated transiently along which the microdroplets can be caused to move.

In our corresponding published patent WO 2018/234448, the entirety of which is incorporated by reference herein, use of this device as an operative part of a nucleic acid sequencer is described.

We have now developed a device for applying microdroplet methods similar to those underpinning our previously described sequencer to the rapid screening and manipulation of biological samples containing cells.

Thus, according to the present invention there is provided a device for manipulating and/or determining one or more characteristics of analysing cells contained within a biological sample, the device comprising:

a sorting component configured to separate cell-containing microdroplets from empty ones into a population of cell-containing first microdroplets;

a microdroplet manipulation component configured to manipulate the first microdroplets using real or virtual electrowetting electrodes, the microdroplet manipulation component including:

a first zone configured to arrange the first microdroplets into an array for optical inspection and, optionally, to introduce a reporter system into each first microdroplet by means of microdroplet merging;

a second zone located within or adjacent the first zone and configured to detect merged microdroplets in one or more detection windows; and optionally a third zone in which microdroplets can be sub-divided and isolated for later recovery from the instrument; and an optical detection system configured to detect an optical signal from the merged microdroplets via the one or more detection windows, wherein, for merged microdroplets, the signal arisesing from an interaction between the reporter system and the cells or an expressed product thereof.

According to another aspect of the present invention, there is provided a method for using a device according to the present invention to manipulate and/or determine one or more characteristics of cell types in a biological sample, the method comprising the steps of: creating from the biological sample aqueous first microdroplets in an immiscible carrier fluid, at least some of which are believed to contain cells of a particular cell type; moving the first microdroplets along a pathway using real or virtual electrowetting electrodes to at least one microdroplet inspection location; and analysing the contents of each microdroplet with an optical detection system to determine one or more characteristics of a cell contained in that microdroplet, the one or more characteristics comprising at least one of: cell morphology, cell motility, or cell membrane integrity.

According to another aspect of the present invention, there is provided a method for using the device of the present invention to manipulate and/or determine one or more characteristics of cell types in a biological sample, the method comprising the steps of: creating from the biological sample aqueous first microdroplets in an immiscible carrier fluid, at least some of which are believed to contain cells of the cell type; moving the first microdroplets along a pathway using virtual electrowetting electrodes to at least one microdroplet-merging location; moving aqueous second microdroplets containing a reporter system characteristic of the cell type whose characteristics are being investigated along a pathway using virtual electrowetting electrodes to the microdroplet merging location; merging the first and second microdroplets at the merging location to produce merged microdroplets; and analysing the contents of each merged microdroplet with an optical detection system and detecting an optical signal characteristic of an interaction between the cell and the reporter system.

The method may initially also comprise one or more sorting, culturing and droplet preparation initial steps. These initial steps may comprise one or more of: (a) separating cell-containing first microdroplets from a population of microdroplets including both cell-containing and empty microdroplets; (b) culturing the population of microdroplets under conditions which cause cell growth and division before or after initial step (a) is carried out; (c) generating the population of microdroplets by severing microdroplets from the biological sample by application of an electrowetting stretching force.

In some embodiments of initial step (c) the microdroplets contain growth medium components severed into an immiscible carrier fluid comprising an oil, thereby creating an emulsion which can be subsequently cultured in initial step (b). In another the microdroplets are severed into air or another gas mixture, for example a mixture of carbon dioxide and nitrogen, and subsequently cultured separately from each other. In some embodiments, it may be advantageous to periodically purge the carrier fluid of gases detrimental to the culturing of the cells.

In one embodiment of initial step (b), culturing of the population of microdroplets is carried out in an emulsion and in the presence of a flowing stream of immiscible carrier fluid such as a hydrocarbon or fluorinated oil, especially a fluorinated oil. This oil may optionally further comprise surfactants and other additives to maintain microdroplet stability. The oil also contains low levels of the nutrients and gases required to maintain cell growth during the culturing phase and application of this embodiment causes the nutrient content of the microdroplets to be either periodically or continuously replenished by interfacial diffusion. Alternatively, nutrient and gaseous replenishment can be achieved directly by the merging of secondary aqueous microdroplets containing these components; for example where the carrier fluid is air or inert gas. In another embodiment the oil is purged of certain dissolved gases in order to provide a hypoxic environment to the cells.

In one embodiment of initial step (b), we have found that in order to maintain cell growth it is necessary to maintain optimum levels of certain atmospheric gases in the microdroplets. Failure to do so can for example cause adverse changes to the pH of the microdroplet medium. Thus in one embodiment initial step (b) the flowing stream of immiscible carrier fluid contains one or more of saturation levels of nitrogen, oxygen or in particular carbon dioxide.

In another embodiment of initial step (b), the contents of the microdroplets are stirred or agitated by application of an electrowetting force at locations where the microdroplets are held. Suitably this is achieved using an optically-mediated electrowetting force delivered for example by an OEWOD structure of the type described below. This approach we believe is also of wider utility and thus in another generally-applicable second aspect of the invention there is provided a method of stirring or otherwise agitating the contents of a microdroplet comprising the steps of: locating the microdroplet at a virtual electrowetting electrode location; and applying a source of electromagnetic radiation to the location thereby activating the corresponding virtual electrowetting electrode and generating an associated electrowetting force characterised in that the source of electromagnetic radiation is moved around the location to cause a corresponding movement of the microdroplet and a corresponding stirring or agitation of its contents.

In some embodiments, the biological sample may comprise one or more male and/or female gametes, and the method may further comprise the manipulation and inspection of the male and/or female gametes as part of in-vitro fertilization workflows.

For example, using the instrument it is possible to conduct inspection, selection and assaying steps on male gamete cells, such as human or animal sperm cells. In one example procedure, a sample of sperm cells is prepared from diluted semen and encapsulated in to droplets. Droplets are loaded on to the chip and then inspected using brightfield microscopy. Those droplets which contain no gametes are then discarded, and any containing sperm cells are retained for inspection. Once a sample of gametes is selected for analysis, videos are taken of the gametes along with still images. Pattern recognition algorithms applied to the output from the optical detection system enable characterisation of the gametes for motility, body morphology and nucleus morphology. The results of this characterisation can be mapped on to a particular droplet which is then retrieved for further processing. This processing includes assaying steps on-chip such as the addition of reporter reagents.

In another example, by encapsulating a female gamete such as a human or animal ovum, it is possible to conduct fertilisation of the ovum. Similarly to the male gamete it is possible to encapsulate the female gamete in a droplet and load in to the chip. Once on the device the cell can be inspected for defects in morphology and assayed with reporter reagents. After inspection or assaying, the female gamete cell could be subjected to optional processing steps, such as the removal of germinal epithelium cells through mechanical shear applied via droplet motion or through the addition of further reagents.

In yet another example, by loading male and female gametes onto a single microfluidic device, it is possible to merge droplets containing the two gametes together and cause them to combine. In one example application a large number of male gamete droplets are merged with a single ovum; conventional interactions between the gametes lead to fertilisation and generation of a blastocyst on-chip. In another example, a single selected male gamete and a single selected and processed female gamete are combined on-chip and are caused to interact.

In another example application, gametes of both sexes are recovered from the microfluidic chip, and are combined using conventional handling techniques known the art such as ICSI or IVF.

In some embodiments, blastocysts, which may be formed through the methods detailed above, or through the conventional means known in the art, can also be encapsulated in droplets and cultured on-chip. On chip culturing allows for the inspection of the blastocyst during formation, using the imaging and detection systems described below. Using droplet merging operations the blastocyst environment can be controlled through the addition of extra materials such as buffer solutions, salts, nutrients, proteins and extracellular matrix materials. During blastocyst formation it is often desirable to use techniques such as laser microdissection to remove a sample of cells from the blastocyst and recover them for further analysis. In some embodiments, the blastocyst is transported to a droplet manipulation zone. This manipulation zone may comprise a physical feature on the microfluidic chip, such as a pillar, post, a physical restriction between the electrowetting plates or a wedge-shaped variation in the gap between the electrowetting plates such as is described in PCT/EP2019/062791, the disclosure of which is incorporated by reference herein. Once a blastocyst is loaded in to the manipulation zone it is effectively held immobile. Laser microdissection can then proceed, the process of which is well described in literature, in order to remove a portion of the blastocyst. Once a portion of the droplet is excised, droplet splitting operations as described herein can be used to separate the sample portion from the blastocyst. Through repeated splitting and re-merging operations and machine-vision inspection of the distribution of material between the two droplets after splitting, it is possible to verify that the blastocyst and the sample portion have been correctly separated. After separation the sample portion of the blastocyst can be recovered for further analysis, such as through a genetic test including polymerase chain reaction or DNA sequencing.

Suitably, the source of electromagnetic radiation used in this method corresponds to the second electromagnetic radiation described below and comprises a source of rapidly flashing rotational light describing a circular pathway within or around the periphery of the location. In another embodiment, the movement of the light source may comprise a pathway of one or more lateral motions. In one manifestation, the locations are defined by areas of at least 0.5 microns in diameter and the motion is circular, radial or a mixture of the two. The motion is radial to generate corresponding centrifugal mixing of the contents of the microdroplet.

The reporter systems which can be introduced into the first microdroplets in step (4) can in principle be any system which is characteristic of or which may be used to assay the presence of a given cell type or cell behaviour in biological sample. Such reporter systems include, for example, a reporter gene, a cell-surface biomarker or a reporter molecule selective for an enzyme, protein or antibody expressed by cells of the cell type being sought. A related class of reporter system can be a second reporter cell which responds to the presence of relevant material expressed by the cell being sought. Many such assays are known and suitable candidates for use will in many cases be apparent to one of ordinary skill in the art. Furthermore it will be appreciated that by introducing a plurality of different reporter systems into the first microdroplets by the merging of one or more second microdroplet types the method may be multiplexed so as to carry out parallel and simultaneous searches for a range different cell types associated with a range of different characteristics and behaviours.

The method of the present invention and its various steps and initial sub-steps can be conveniently carried out using an analytical device of the type described below. Examples of the optical detection system applicable to the method are also described below. In some embodiments, this device comprises:
  a sorting component for separating cell-containing microdroplets from empty ones into a population of cell-containing first microdroplets;
  a microdroplet manipulation component for subsequently manipulating the first microdroplets using real or virtual electrowetting electrodes and including:
    a first zone including a means for introducing a reporter system into each first microdroplet by means of microdroplet merging;
    a second zone located within or adjacent the first zone in which merged microdroplets are thereafter detected in one or more detection windows and
  an optical detection system for detecting an optical signal from the merged microdroplets arising from an interaction between the reporter system and the cells or an expressed product thereof selected from a brightfield microscope, a darkfield microscope, a means for detecting chemiluminescence, a means for detecting Förster resonance energy transfer or a means for detecting fluorescence.

The sorting component employed in such embodiments is a means for separating microdroplets containing one or more cells (hereinafter 'filled microdroplets') from a larger population some of which are empty. Depending on the type of sorting component chosen, the microdroplets are directed down or towards one of two different microfluidic pathways or receiving locations depending on whether they are filled or empty. In some embodiments, access to one or other of these is controlled by a divider or actuation of an electromechanical gate acting in response to the analysis of each microdroplet in an analytical window. In another embodiment, sorting is accomplished by applying a responding optically-mediated electrowetting force in the analytical window to a stream of the microdroplets so that the chosen ones are pulled into a holding area or array. The rejected microdroplets then remain in the stream and thereafter can be discarded. In another, embodiment, the sorting decision is based on an optical phenomenon; for example brightfield microscopy or by detecting an optical property associated with the cells e.g. the presence of a fluorescent tag or marker. In another embodiment, sorting may be achieved by a dielectrophoretic method in which a temporary electric field is applied in the analytical window to deflect each microdroplet in turn towards one of two different pathways either side of a divider. In one embodiment, the sorting component comprises a first microfluidic channel terminating in analytical chamber; at least two second microfluidic channels connected to the analytical chamber on the downstream side at least one of which carries away the first microdroplets, a light source for illuminating the analytical chamber; a brightfield microscope or fluorescence detector for obtaining data from each illuminated microdroplet in the analytical chamber; at least one OEWOD structure operable to direct the microdroplets down one of the two second channels and a microprocessor adapted to operate the structure(s) in response to a result from an identification algorithm applied to data received from the microscope or fluorescence analyser.

In one embodiment, the device further comprises a culturing-component which is either an integral component of the device itself or separately located before or after the sorting component; preferably after the sorting component. Here, the microdroplets are held whilst any cells contained within are cultured so as to stimulate cell division and growth. Suitably, the culturing component comprises a vessel in which the microdroplets are held under optimal culturing conditions; typically from between an hour and a week at a temperature in the range above 25° C. (e.g. 25 to 40° C.) and an inlet port for introducing the microdroplets thereinto. In one embodiment, the culturing component further comprises a thermostatically-controlled heater and optionally a timer which controls filling and discharge cycles for the device. In one embodiment, the contents of the device comprises an emulsion of microdroplets in an immiscible carrier fluid and the device further comprises an inlet and outlet through which carrier fluid can be passed allowing it to be replaced over time. In one embodiment, the immiscible carrier fluid is a fluorocarbon oil such as HFE7500, HFE7700 or FC-40. Such oils suitably further contain surfactants and other additives to maintain microdroplet stability and low levels of the nutrients and gases required to maintain growth.

In one embodiment, of particular utility where the weight ratio of aqueous microdroplets to oil is low, there is a tendency for the microdroplets to shrink over time; a phenomenon which can lead to a loss of reactivity within them. One way of counteracting this effect is to use an oil which has been hydrated. Since generally the oils described above do not have a high capacity for dissolving water, hydration is suitably achieved by creating micelles or secondary microdroplets of water or aqueous buffer within the oil phase. This buffer may have a composition which is the same as or different to that of the microdroplets themselves. In some embodiments these micelles or secondary microdroplets may contain up to five times the salt content of the microdroplets themselves and optionally contain glycerol. Typically these micelles and secondary microdroplets are an order of magnitude smaller.

In one embodiment, the vessel further comprises a surface provided with a plurality of locations at which the microdroplets can be located and agitated to stir their contents using optically mediated electrowetting forces; also as described above.

The device further comprises a sample preparation component either integral with the device itself or separately located upstream of the culturing component which comprises a means for creating an emulsion of the microdroplets in an immiscible carrier fluid from an aliquot of the biological sample.

This sample preparation component includes a severing means for severing microdroplets from the biological sample into the carrier fluid which comprises at least one location where an electrowetting stretching force is applied to the biological sample. In one embodiment the severing means comprises:
 a first electrowetting location adapted to receive the biological sample;
 at least one second electrowetting location arranged so that the first and second electrowetting electrode locations define a pathway along which microdroplets severed from the sample can be transported using directional electrowetting forces;
 an AC drive circuit arranged at the first electrowetting location and comprised of either an electrode and an associated AC electrical circuit or a semiconductor zone activated by the impingement of electromagnetic light thereon and
 a DC charging circuit arranged at the first electrowetting location and adapted to electrostatically charge the surface of the biological sample.

In one embodiment, the severing means further comprises a control circuit for switching between the drive and charging circuits which are suitably AC and DC circuits respectively. In another embodiment, the severing means further comprises an analyser for analysing the contents of each microdroplet produced from the biological sample. In this respect, the biological sample can be in the form of any aqueous material such as blood, plasma, sputum, urine or material derived from tissue biopsies. Further information about suitable severing means can be found in our co-pending application EP18201162.7 to which the reader is directed. It will be readily appreciated that microdroplet-severing method associated with this severing means can form the basis of carrying out initial step (c) above.

Turning to the microdroplet manipulation component which is used to subsequently manipulate the first microdroplets produced by the sorting component, this is suitably a microfluidic chip comprised of a first zone, a second zone and an optical detection system comprised of real or virtual electrowetting electrodes, linked together by one or more microfluidic pathways along which the first microdroplets are driven by pneumatic and/or electrowetting forces. Suitably, the electrowetting electrodes are virtual and established at locations in one or more OEWOD structures. Generally, this is the way of manipulating the microdroplets in the method and in one embodiment these OEWOD structures are comprised of:
 a first composite wall comprised of:
  a first substrate
  a first transparent conductor layer on the substrate, the first transparent conductor layer having a thickness in the range 70 to 250 nm;
  a photoactive layer activated by electromagnetic radiation in the wavelength range 400-850 nm on the conductor layer, the photoactive layer having a thickness in the range 300-1500 nm and
  a first dielectric layer on the photoactive layer, the first dielectric layer having a thickness in the range 30 to 160 nm;
 a second composite wall comprised of:
  a second substrate;
  a second conductor layer on the substrate, the second conductor layer having a thickness in the range 70 to 250 nm and
  optionally a second dielectric layer on the second conductor layer, the second dielectric layer having a thickness in the range 30 to 160 nm
 wherein the exposed surfaces of the first and second dielectric layers are disposed 20-180 μm apart to define a microfluidic space adapted to contain microdroplets;
 an A/C source to provide a voltage across the first and second composite walls connecting the first and second conductor layers;
 at least one source of electromagnetic radiation having an energy higher than the bandgap of the photoactive layer adapted to impinge on the photoactive layer to induce corresponding virtual electrowetting locations on the surface of the first dielectric layer; and
 means for manipulating the points of impingement of the electromagnetic radiation on the photoactive layer so as to vary the disposition of the virtual electrowetting locations thereby creating at least one electrowetting pathway along which the microdroplets may be caused to move.

In one embodiment, the first and second walls of these structures are transparent with the microfluidic space sandwiched in-between. In another, the first substrate and first conductor layer are transparent enabling light from the source of electromagnetic radiation (for example multiple laser beams, a lamp or an LED) to impinge on the photoactive layer. In another, the second substrate, second conductor layer and second dielectric layer are transparent so that the same objective can be obtained. In yet another embodiment, all these layers are transparent.

Suitably, the first and second substrates are made of a material which is mechanically strong for example glass metal or an engineering plastic. In one embodiment, the substrates may have a degree of flexibility. In yet another embodiment, the first and second substrates have a thickness in the range 100-1000 µm. In some embodiments the first substrate is comprised of one of Silicon, fused silica, and glass. In some embodiments, the second substrate is comprised of one of fused silica and glass.

The first and second conductor layers are located on one surface of the first and second substrates and typically have a thickness in the range 70 to 250 nm, preferably 70 to 150 nm. In one embodiment, at least one of these layers is made of a transparent conductive material such as Indium Tin Oxide (ITO), a very thin film of conductive metal such as silver or a conducting polymer such as PEDOT or the like. These layers may be formed as a continuous sheet or a series of discrete structures such as wires. Alternatively, the conductor layer may be a mesh of conductive material with the electromagnetic radiation being directed between the interstices of the mesh.

The photoactive layer is suitably comprised of a semiconductor material which can generate localised areas of charge in response to stimulation by the source of the second electromagnetic radiation. Examples include hydrogenated amorphous silicon layers having a thickness in the range 300 to 1500 nm. In one embodiment, the photoactive layer is activated by the use of visible light.

The photoactive layer in the case of the first wall and optionally the conducting layer in the case of the second wall are coated with a dielectric layer which is typically in the thickness range from 30 to 160 nm. The dielectric properties of this layer preferably include a high dielectric strength of >10^7 V/m and a dielectric constant of >3. Preferably, it is as thin as possible consistent with avoiding dielectric breakdown. In one embodiment, the dielectric layer is selected from alumina, silica, hafnia or a thin non-conducting polymer film.

In another embodiment of these structures, at least the first dielectric layer, preferably both, are coated with an anti-fouling layer to assist in the establishing the desired microdroplet/carrier fluid/surface contact angle at the various virtual electrowetting electrode locations, and additionally to prevent the contents of the microdroplets adhering to the surface and being diminished as the microdroplet is moved through the chip. If the second wall does not comprise a second dielectric layer, then the second anti-fouling layer may be applied directly onto the second conductor layer. For optimum performance, the anti-fouling layer should assist in establishing a microdroplet/carrier fluid/surface contact angle that should be in the range 50-170° when measured as an air-liquid-surface three-point interface at 25° C. In one embodiment, these layer(s) have a thickness of less than 10 nm and are typically a monomolecular layer. In another, these layers are comprised of a polymer of an acrylate ester such as methyl methacrylate or a derivative thereof substituted with hydrophilic groups; e.g. alkoxysilyl. Either or both of the anti-fouling layers are hydrophobic to ensure optimum performance. In some embodiments an interstitial layer of silica of thickness less than 20 nm may be interposed between the anti-fouling coating and the dielectric layer in order to provide a chemically compatible bridge.

The first and second dielectric layers, and therefore the first and second walls, define a microfluidic space which is at least 10 µm, and preferably in the range of 20-180 µm, in width and in which the microdroplets are contained. Preferably, before they are contained, the microdroplets themselves have an intrinsic diameter which is more than 10% greater, suitably more than 20% greater, than the width of the microdroplet space. By this means, on entering the chip the microdroplets are caused to undergo compression leading to enhanced electrowetting performance through e.g. a better microdroplet merging capability.

In one embodiment the first and second dielectric layers are coated with a hydrophobic coating such a fluorosilane.

In another embodiment, the microfluidic space includes one or more spacers for holding the first and second walls apart by a predetermined amount. Options for spacers include beads or pillars, ridges created from an intermediate resist layer which has been produced by photo-patterning. Alternatively, deposited material such as silicon oxide or silicon nitride may be used to create the spacers. Alternatively layers of film, including flexible plastic films with or without an adhesive coating, can be used to form a spacer layer. Various spacer geometries can be used to form narrow channels, tapered channels or partially enclosed channels which are defined by lines of pillars. By careful design, it is possible to use these spacers to aid in the deformation of the microdroplets, subsequently perform microdroplet splitting and effect operations on the deformed microdroplets. Similarly these spacers can be used to physically separate zones of the chip to prevent cross-contamination between droplet populations, and to promote the flow of droplets in the correct direction when loading the chip under hydraulic pressure.

The first and second walls are biased using a source of A/C power attached to the conductor layers to provide a voltage potential difference therebetween; suitably in the range 10 to 50 volts.

These OEWOD structures are typically employed in association with a source of second electromagnetic radiation having a wavelength in the range 400-850 nm, preferably 660 nm, and an energy higher than the bandgap of the photoactive layer. Suitably, the photoactive layer will be activated at the virtual electrowetting electrode locations where the incident intensity of the radiation employed is in the range 0.01 to 0.2 $Wcm^{-2}$. The source of electromagnetic radiation is, in one embodiment, pixelated so as to produce corresponding photoexcited regions on the photoactive layer which are also pixelated. By this means, pixelated virtual electrowetting electrode locations are induced on the first dielectric layer.

Where the source of electromagnetic radiation is pixelated it is suitably supplied either directly or indirectly using a reflective screen such as a digital micromirror device (DMD) illuminated by light from LEDs or other lamps. This enables highly complex patterns of virtual electrowetting electrode locations to be rapidly created and destroyed on the first dielectric layer thereby enabling the microdroplets to be precisely steered along essentially any virtual pathway using closely-controlled electrowetting forces. This is also especially advantageous where there is a requirement for the chip to manipulate many thousands of such microdroplets simultaneously along multiple pathways. Such electrowetting pathways can be viewed as being constructed from a continuum of virtual electrowetting electrode locations on the first dielectric layer.

The points of impingement of the sources of electromagnetic radiation on the photoactive layer can be any convenient shape including the conventional circular or annular. In one embodiment, the morphologies of these points are determined by the morphologies of the corresponding pixelations and in another correspond wholly or partially to the morphologies of the microdroplets once they have entered the microfluidic space. In one embodiment, the points of impingement and hence the electrowetting electrode locations may be crescent-shaped and orientated in the intended direction of travel of the microdroplet. Suitably the electrowetting electrode locations themselves are smaller than the microdroplet surface adhering to the first wall and give a maximal field intensity gradient across the contact line formed between the droplet and the surface dielectric.

In one embodiment of the OEWOD structure, the second wall also includes a photoactive layer which enables virtual electrowetting electrode locations to also be induced on the second dielectric layer by means of the same or different source of electromagnetic radiation. The addition of a second dielectric layer enables transition of the wetting edge of a microdroplet from the upper to the lower surface of the structure, and the application of more electrowetting force to each microdroplet.

The first zone which forms part of the device is in one embodiment, a holding reservoir comprising an inlet for introducing the first microdroplets and an outlet attached by an electrowetting pathway to the second zone. The first zone further includes a port for introducing a reporter system which in one suitable embodiment is a second inlet for introducing second aqueous microdroplets containing a reporter system designed to identify the nature of the cells contained in the first microdroplets. In one embodiment the reservoir further includes an array of locations where the first microdroplets can be held whilst the second microdroplets are driven over them; in the process causing a degree of merging of the first and second microdroplets. The merged first/second microdroplets (hereinafter 'merged microdroplets') can then be held at the locations until the reporter system has interacted sufficiently with cells to subsequently generate an optimum optical signal at which time they are transported to the second zone by electrowetting. In some instances it may be desirable to monitor the growth of the optical signal using time-resolved measurements. In one embodiment, a single zone encompassing the duties of both the first and second zones is employed; for example by detecting the merged microdroplets at the merging locations referred to above.

The second zone is suitably comprised of one or more detection windows through which the merged microdroplets can be analysed using an optical detection system. In one embodiment. the second zone is a transparent section of the chip. In another embodiment, the optical detection system is one designed to detect an optical signal from the microdroplets arising from an interaction between the reporter system and the cells or an expressed product thereof. Suitably, the optical detection system is selected from a brightfield microscope, darkfield microscope, a means for detecting chemiluminescence, a means for detecting Förster resonance energy transfer or a means for detecting fluorescence. In one embodiment, the detection system also includes a source of light to illuminate the merged microdroplets and/or a microprocessor for receiving a signal from one of the detectors and providing data to a user in the form of, for example, a visual display or count. In one embodiment, the microprocessor is further adapted by means of a feedback loop to control one or more of the performance of the sorting component; the rate of introduction of the first microdroplets into the first zone and the rate of merging of the first and reporter system-containing microdroplets in response to a signal detected by the optical detection system.

A particular advantage of an instrument using oEWOD structures for performing the droplet manipulations is that an optical addressing system focused on the sample is built in to the instrument. By multiplexing and de-multiplexing the excitation and emission light required for optical detection in with the illumination required for oEWOD control, it is possible to consolidate many of the optical functions into one simpler and lower cost assembly. For example, it is possible to de-multiplex luminescence emission from the assembly using a long-pass dichroic mirror to divert light from the manipulation column and to a high-sensitivity detection camera. Another embodiment uses two dichroic mirrors; a first mirror to multiplex in fluorescence excitation light from a lamp and a second to de-multiplex fluorescence emission. For embodiments requiring more sophisticated illumination schemes such as time-resolved Förster resonance energy transfer it is favourable to employ the same structured illumination system which addresses the oEWOD manipulation patterns to apply a time-dependent and spatially varying illumination pattern. As well as using dichroic mirrors for these multiplexing operations it is possible to use elements such as dispersive filters, dispersive lenses or gratings. For some applications it is favourable to perform temporal multiplexing whereby the structured illumination system is used to switch rapidly between excitation sources.

In some embodiments, the device further comprises a third zone for recovering microdroplets from the first and/or second zones. Here, the first microdroplets can be subdivided and isolated for later recovery from the instrument; for example for more detailed or and a confirmatory analysis. In one embodiment, the third zone is comprised of one or more outlet ports from the second zone connected to a temporary storage vessel. By replenishing the first and second zones using the oEWOD transport mechanism, it is possible to perform many recoveries of microdroplets in sequence, enabling multiple droplets to be separately recovered from one port.

As well as the optically mediated manipulation of fluids in the OEWOD structure, the device may also include a network of pumps and valves to manipulate the flow inside the device by selective application of hydraulic pressure to the various inlet and outlet ports. Preferably, this network comprises two-position valves connected to each outlet and a set of pressure sources (such as pumps), collection vessels and reservoirs connected to the same valves. By changing the configuration of each valve, it is possible to apply positive or negative pressure within the device via the reservoirs and collection vessels and hence cause the flow of material into, out of or within the device.

The device and associated methods of the present invention described above have numerous beneficial applications. Some example applications and associated workflows are described below.

One example application of the disclosed device and methods is the development of genetically modified cell lines.

In this application, target cells are encapsulated in first microdroplets via the optically mediated electrowetting based severing means of the sample preparation component. Transfection reagents such as, for example, a modified lentivirus, are encapsulated in separate second microdroplets.

The first and second microdroplets are then merged on the OEWOD device in a merging operation as described above to form merged microdroplets, causing the target cells to be exposed to the transfection reagents. Cells in the merged microdroplets are put through cycles of merging and splitting operations in which the cell population is divided amongst droplets, and the media surrounding the cells is exchanged with fresh media through serial dilution, replenishing depleted material and removing any cell excreta that has accumulated within the droplets.

Tracking the location of each cell in the microdroplet population, for example by microscopic inspection during the assay, enables cells from common ancestors to be identified for sorting purposes, ensuring monoclonality of cultured cell populations.

Cell-retention is also increased compared to conventional methods of cell line development, as during the described process there are no harmful steps of freeze-thawing, dispensing, manual handling or repeated long-term passaging that are known to reduce the viability of cells. Similarly, keeping the cells encapsulated in droplets removes the possibility of losing clones to liquid handling instrument surfaces. Furthermore, non-viable cells can be discovered early on in the process and replaced with viable cells instead.

Once it is determined that the cells in the merged microdroplets have been cultured for a sufficient length of time, a third reagent comprising a reporter assay is introduced to the OEWOD device and merged with the microdroplets containing the target cells. The outcome of the reporter assay may be measured according to, for example, a detected fluorescence, chemiluminescence, or Förster resonance energy transfer.

Based on the outcome of the reporter assay, one or more first subsets of the cells may be discarded and one or more second subsets of cells may be caused to proliferate further. A sample is retrieved from the cultured target cell subset and dispensed from the chip into a well-plate, for example, a standard 1536 well plate, for further analysis off-chip. The remaining progenitor cells of the cultured subset are retained for further culturing on-chip.

The retrieved sample is then subjected to one or more off-chip analyses, such as: DNA sequencing, RNA sequencing, PCR analysis, genetic profiling, and micro-array measurement. A further subset of the cells on-chip may be selected, retrieved, and cultured further on the basis of the outcome of the off-chip analysis.

Another example application of the present invention is to screen cells for immune functionality.

After immunization with an antigen such as a toxin or a biomarker characteristic of a disease, a sample of native immune-cells such as B-cells, T-cells or dendritic cells may be harvested from an organism such as a mouse, human, or primate. The cells are then treated and purified in order to separate them from surrounding tissue, lymph, blood cells and other components from the host organism. This can be achieved through a mixture of dissection, centrifugation, immunoprecipitation, filtration and dialysis.

The purified immune cells are encapsulated in microdroplets and loaded onto the OEWOD device. A reagent such as an immunoassay reagent, a FRET reporter, or a reporter cell line is then introduced to the microdroplets containing the target cells in a first assay. This may be performed as described above by creating second microdroplets of the reagent and carrying out a merging operation.

The result of the first assay is interrogated, for example by optical detection or microscopic inspection, to determine whether proteins such as antibodies are excreted by the target cells in response to the immunoassay reagent. Based on the outcome of the first assay, a subset of the microdroplets containing the target cells may be discarded from the device, and another subset is retained for further testing.

A second reagent, such as an off-target reporter, may then be introduced in a similar manner to the remaining cell-containing microdroplets in a second on-chip assay. The outcome of the second assay is measured with an optical technique such as fluorescence spectroscopy, leading to a second round of selection and discarding of microdroplet subsets. The above process may be repeated to interrogate/screen the target cells using a series of different reporter assays, measuring the response of the target cells to on-targets, off-targets, and irrelevant targets.

As used herein, the term "on-target" refers to a tissue or antigen of interest, and to which the target cell is producing response antibodies such as. For example, an on-target may be a cancerous tissue. As used herein, the term "off-target" refers to a tissue in which undesirable effects are observed or expected. An example off-target may be a healthy tissue which is near to or associated with a cancerous tissue. As used herein, the term "irrelevant target" refers to material which is expected to have no biological interaction with an antibody, but which could have a negative effect on the accuracy of the assay results by, for example, binding large amounts of the antibody to no useful end, or confounding measurements.

Based on the measured outcomes of the screening assays, a final subset of the cells are selected. The remaining cell-containing microdroplets containing the final subset are then introduced to a selected lysis reagent and cDNA synthesis reagent in order to form a library of genes currently being expressed in the target cell. The cells of interest are recovered off-chip and subjected to a genetic assay which indicates the coding DNA responsible for the behaviours observed in the on-chip phenotypic assays.

Another example application of the present invention is screening for drug functionality and efficacy, including immunomodulation drugs and drugs for tumor suppression.

In this application, a panel of drug-target cells are encapsulated in first microdroplets and loaded on to the OEWOD device. A set of second microdroplets comprising a panel of drug compounds for testing is also loaded on.

Dosimetry panels are formed from by merging and splitting operations performed on the second microdroplets to create panels of microdroplets containing a range of dilutions of the respective drug compounds. The drugs compounds may be in the form of micro-beads, encapsulated in vesicles, or expressed by production cells encapsulated in the droplets.

The drug dosimetry panels are introduced to the target cells through merging operations; an exhaustive pair-wise combination process between the first cell containing microdroplets and the microdroplets of the drug dosimetry panels ensures that the whole panels are exposed to every cell type in replicate. An effector cell, such as for example a T-killer cell or Macrophage, can also be introduced along with the drug panel and the target cell in order to test the effect of the drug in modulating the immune response, and to make a detailed cross comparison of the immune response in the presence of different tissues.

The response of the target cells to the drug panels may be monitored through, for example, microscopic inspection, fluorescent reporter stains or a reporter assay. The result of the screening process can be used to inform on the potency of the tested drugs in various cell and effector cell conditions.

Another example application of the present invention is in inducing differentiation of target stem cells.

In this application, target stem cells such as for example induced pluripotent stem cells, embryonic stem cells, Mesenchymal stem cells or Hematopoietic stem cells, are encapsulated in first microdroplets and loaded onto the OEWOD device.

A panel of controlling reagent compounds, such as for example growth factors, environmental stimulants, cell to cell signaling compounds, and morphogens, are encapsulated into second microdroplets and also loaded onto the OEWOD device.

A subset of the first microdroplets are merged with the second microdroplets containing the control reagents in order to expose the stem cells contained in the first microdroplets to the reagents and thus promote the differentiation of the stem cells along target pathways.

The stem cell differentiation process is monitored through, for example microscope imaging, detection of phenotypic reporter compounds, and by performing reporter assays. The differentiated cells in the merged microdroplets can be recovered from the OEWOD device via a dispense step for further culturing or processing.

Yet another example application of the present invention is in the controlled formation of organoid structures.

In this application, organoid progenitor cells, such as for example tumor cells or stem cells, are encapsulated into first microdroplets and loaded on to the OEWOD device. A panel of controlling reagents such as for example growth factors, environmental stimulants, cell to cell signaling compounds, and morphogens, are encapsulated into second microdroplets and also loaded onto the OEWOD device.

A subset of the organoid progenitor cell population contained in the first microdroplets is exposed to the control reagents via a merging operation in order to promote the formation of organoids and tissue structures. Organoids thus formed can be stored in a dedicated area on-chip on the OEWOD device and supplied with nutrients and any other required growth media via droplet merging operations. Organoids stored on chip in this manner can be subjected to drug-screening assays as described in relation to the above example applications.

Another example application of the present invention is in CRISPR-Cas9 genetic modification screening.

In this application, target cells are encapsulated in first microdroplets and loaded on to the OEWOD device. A second set of microdroplets comprising a panel of gRNA-pairs is also loaded onto the device. Loading the panel of gRNA-pairs may involve a preparatory step of spotting lyophilized gRNAs onto target regions of the device surface and subsequently re-hydrating the regions comprising the panel by causing microdroplets to pass over them.

This may be in the form of a bead-prep step in which gRNAs are bound to microbeads and these beads are spotted and lyophilized on to the surface of the fluidic.

The gRNAs are introduced to the target cells via merging operations, which cause the target cells to take up the gRNA along with a programmable restriction enzyme such as Cas9 and also the required reagents for inducing a genetic modification in the target cell.

Cells in the merged microdroplets are put through cycles of merging and splitting operations in which the cell population is divided amongst droplets, and the media surrounding the cells is exchanged through serial dilution.

Tracking the location of each cell in the microdroplet population enables cells from common ancestors to be identified for sorting purposes, increasing monoclonality of cultured cell populations. Cell-retention is also increased.

Once it is determined that the cells in the merged microdroplets have been cultured for a sufficient length of time, a third reagent comprising a reporter assay is introduced to the OEWOD device and merged with the microdroplets containing the target cells. The outcome of the reporter assay may be measured according to, for example, a detected fluorescence, chemiluminescence, or Förster resonance energy transfer.

Based on the outcome of the reporter assay, one or more first subsets of the cells may be discarded and one or more second subsets of cells may be caused to proliferate further. A sample is retrieved from the cultured target cell subset and dispensed from the chip into a well-plate, for example, a standard 1536 well plate, for further analysis off-chip. The remaining progenitor cells of the cultured subset are retained for further culturing on-chip.

The retrieved sample is then subjected to one or more off-chip analyses, such as: DNA sequencing, RNA sequencing, PCR analysis, genetic profiling, and micro-array measurement. A further subset of the cells on-chip may be selected, retrieved, and cultured further on the basis of the outcome of the off-chip analysis.

An example device and associated example workflow is now illustrated with reference to FIG. 1.

A fluid inlet 1 admits an emulsion 2 of a mixture of empty and cell-containing first microdroplets in a fluorocarbon oil. These first microdroplets are then transferred by means of OEWOD structures (not shown) to a sorting zone 3 where they are sorted, by optical means or by other sorting means as described above, into those which are empty 4 and those which contain cells 5. Thereafter each of the cell-containing microdroplets 5 are transferred to merging zone 8, also by means of OEWOD structures, where they are held for a defined period of time under conditions which promote cell growth and division within each. At the end of this period, a second inlet 6 admits second microdroplets, containing a fluorescence reporter system selective for a cell type of interest 7 which are then merged with the cell-containing first microdroplets 5 at merging zone 8 to form merged microdroplets 9. The merged microdroplets 9 are then transferred by means of OEWOD structures to optical window 10 where a fluorescence signal characteristic of the reporter system is detected using an optical detection instrument 11 comprised of an LED light source, a photodetector and a microprocessor. Optical detection instrument 11 is partially combined with an optical manipulation projector 12.

Figure 2:
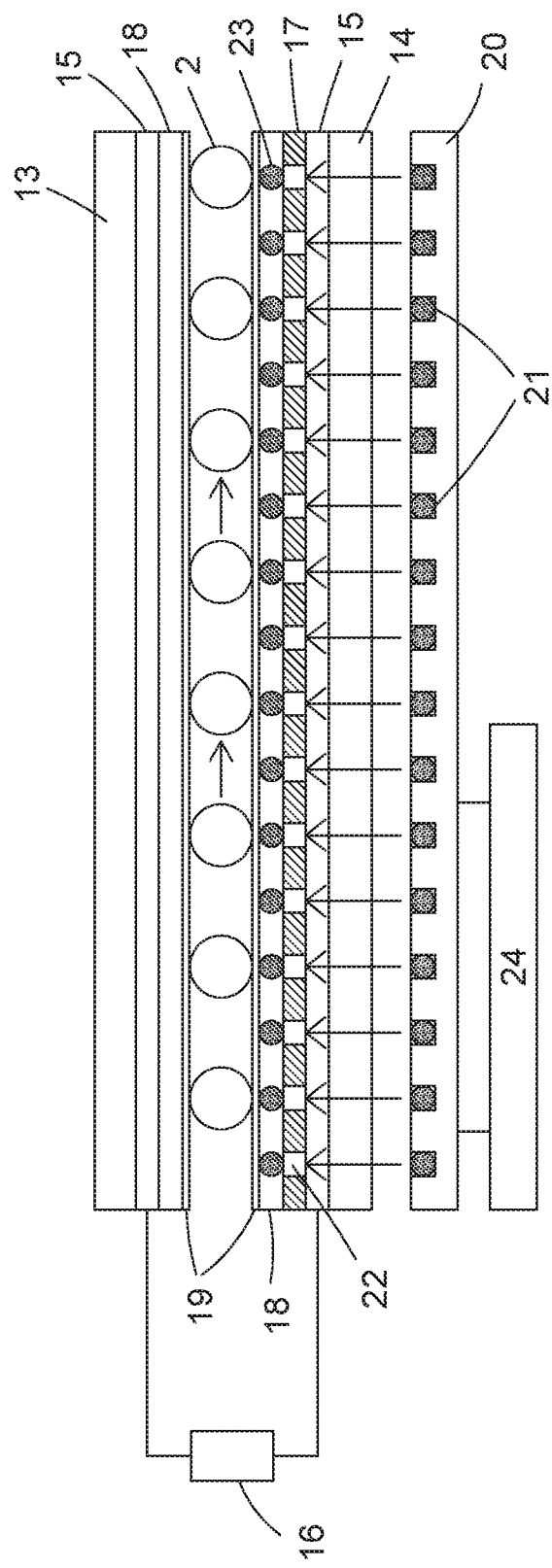

FIG. 2 shows a cross-sectional view of an example device comprising an oEWOD structure suitable for the fast manipulation of aqueous microdroplets 2 emulsified into a fluorocarbon oil having a viscosity of 5 centistokes or less at 25° C. and which in their unconfined state have a diameter of 120 µm (e.g. in the range 80 to 120 µm). It comprises top and bottom glass plates (13 and 14) each 500 µm thick coated with transparent layers of conductive Indium Tin Oxide (ITO) 15 having a thickness of 130 nm. Each of 15 is connected to an A/C source 16 with the ITO layer on 14 being the ground. 14 is coated with a layer of amorphous silicon 17 which is 800 nm thick. 13 and 17 are each coated with a 160 nm thick layer of high purity alumina or Hafnia 18 which are in turn coated with an interstitial layer of silicon dioxide supporting a layer of Trichloro(1H,1H,2H,2H-perfluorooctyl)silane 19 to render the surfaces of 18 hydrophobic. 13 and 17 are spaced 80 µm apart using spacers so that the microdroplets undergo a degree of compression when introduced into the device. An image of a reflective pixelated screen, illuminated by an LED light source 20 is disposed generally beneath 14 and visible light (wavelength 660 or 830 nm) at a level of 0.01 $Wcm^{-2}$ is emitted from each diode 21 and caused to impinge on 17 by propagation in the direction of the multiple upward arrows through 14 and 15. At the various points of impingement, photoexcited regions of charge 22 are created in 17 which induce modified liquid-solid contact angles in 18 at corresponding electrowetting locations 23. These modified properties provide the capillary force necessary to propel the microdroplets 2 from one point 23 to another. 20 is controlled by a microprocessor 24 which determines which of 21 in the array are illuminated at any given time by preprogrammed algorithms.

The invention claimed is:

1. A device for manipulating and/or determining one or more characteristics of cells contained within a biological sample, the device comprising:
    a sorting component configured to separate cell-containing microdroplets from empty ones into a population of cell-containing first microdroplets;
    a microdroplet manipulation component configured to manipulate the first microdroplets using real or virtual electrowetting electrodes, the microdroplet manipulation component including:
        a first zone configured to arrange the first microdroplets into an array for optical inspection and, optionally, to introduce a reporter system into each first microdroplet by means of microdroplet merging;
        a second zone located within or adjacent the first zone and configured to detect merged microdroplets in one or more detection windows; and
        optionally a third zone in which microdroplets can be sub-divided and isolated for later recovery from the instrument; and
    an optical detection system configured to detect an optical signal from the microdroplets via the one or more detection windows, wherein, for merged microdroplets, the signal arises from an interaction between the reporter system and the cells or an expressed product thereof.

2. A device as claimed in claim 1, wherein the optical detection system is selected from: a brightfield microscope, a darkfield microscope, a means for detecting chemiluminescence, a means for detecting Förster resonance energy transfer, and a means for detecting fluorescence.

3. A device as claimed in claim 1, further comprising a cell-culturing component, either integral with the device or separately located before or after the sorting component, configured to hold the microdroplets whilst any cells contained within are cultured.

4. A device as claimed in claim 3, wherein the cell-culturing component is further configured to agitate the contents of each microdroplet using optically-mediated electrowetting forces.

5. A device as claimed in claim 3, wherein the device further comprises a heater and temperature controller configured to control the temperature of the microdroplets in the cell-culturing component within the range 25 to 40° C.

6. A device as claimed in claim 1, further comprising a sample preparation component, either integral with the device or separately located before the sorting component, configured to create an emulsion of the microdroplets in an immiscible carrier fluid from the biological sample.

7. A device as claimed in claim 3, wherein at least one of the sorting component, the cell-culturing component and a sample preparation component is configured with electrowetting electrode locations to enable the droplets to be manipulated therein and/or therebetween.

8. A device as claimed in claim 6, wherein the sample preparation component includes at least one location where an electrowetting stretching force is applied to the biological sample, and is configured to sever microdroplets from the biological sample into the carrier fluid.

9. A device as claimed in claim 1, wherein the optical detection means comprises a source of first electromagnetic radiation adapted to impinge on the first microdroplets in the one or more detection windows, and further comprises a detector for detecting fluorescence emitted from the microdroplets.

10. A device as claimed in claim 1, wherein the microdroplet manipulation component includes one or more OEWOD structures comprised of:
    a first composite wall comprised of:
        a first substrate
        a first transparent conductor layer on the substrate, the first transparent conductor layer having a thickness in the range 70 to 250 nm;
        a photoactive layer activated by electromagnetic radiation in the wavelength range 400-850 nm on the conductor layer, the photoactive layer having a thickness in the range 300-1500 nm and
        a first dielectric layer on the photoactive layer, the first dielectric layer having a thickness in the range 30 to 160 nm;
    a second composite wall comprised of:
        a second substrate;
        a second conductor layer on the substrate, the second conductor layer having a thickness in the range 70 to 250 nm and
        optionally a second dielectric layer on the second conductor layer, the second dielectric layer having a thickness in the range 30 to 160 nm
    wherein the exposed surfaces of the first and second dielectric layers are disposed 20-180 μm apart to define a microfluidic space adapted to contain microdroplets;
    an A/C source to provide a voltage across the first and second composite walls connecting the first and second conductor layers;
    at least one source of electromagnetic radiation having an energy higher than the bandgap of the photoactive layer adapted to impinge on the photoactive layer to induce corresponding virtual electrowetting locations on the surface of the first dielectric layer; and
    means for manipulating the points of impingement of the electromagnetic radiation on the photoactive layer so as to vary the disposition of the virtual electrowetting locations thereby creating at least one electrowetting pathway along which the microdroplets may be caused to move.

11. A device as claimed in claim 10, wherein at least the surface of the first dielectric layer is provided with an anti-fouling coating.

12. A device as claimed in claim 1, wherein the first zone includes a reservoir comprising an array of first microdroplet-holding sites and a port for introducing second microdroplets containing the reporter system, the first zone being further configured to drive the second microdroplets across the first microdroplet-holding sites so that first and second microdroplets are caused to merge.

13. A device as claimed in claim 12, wherein the device is configured to drive the second microdroplets across the first microdroplet-holding sites via one or more pathways of virtual electrowetting electrodes.

14. A device as claimed in claim 12, wherein the device is configured to introduce microdroplets to a first region of the device, connected to the port, in a continuous hydraulic flow, and wherein a second region of the device, overlapping the first region, is configured to channel microdroplets from the first region into a third region of the device for further operations.

15. A device as claimed in claim 1, further comprising a microprocessor adapted by means of a feedback loop to control one or more of the performance of the sorting component; the rate of introduction of the first microdroplets into the first zone and the rate of merging of the first and second microdroplets in response to a signal supplied by the detection system.

16. A device as claimed in claim 1, further comprising an optical assembly configured to illuminate the device and to detect signals characterising cells within the device.

17. A method for using the device of claim 1 to manipulate and/or determine one or more characteristics of cell types in a biological sample, the method comprising the steps of:
creating from the biological sample aqueous first microdroplets in an immiscible carrier fluid, at least some of which are believed to contain cells of a particular cell type;
moving the first microdroplets along a pathway using real or virtual electrowetting electrodes to at least one microdroplet-merging location;
moving aqueous second microdroplets containing a reporter system characteristic of the cell type whose characteristics are being investigated along a pathway using real or virtual electrowetting electrodes to the microdroplet merging location;
merging the first and second microdroplets at the merging location to produce merged microdroplets; and
analysing the contents of each merged microdroplet with an optical detection system and detecting an optical signal characteristic of an interaction between the cell and the reporter system.

18. A method as claimed in claim 17, wherein the step of creating the first microdroplets further comprises separating cell-containing first microdroplets from a population of microdroplets including both cell-containing and empty microdroplets.

19. A method as claimed in claim 17, wherein the step of creating the first microdroplets further comprises culturing the population of microdroplets under conditions which cause cell growth and division.

20. A method as claimed in claim 19, wherein culturing the population of microdroplets comprises contacting the population of microdroplets in the immiscible carrier fluid with a flow of carrier fluid containing cell-culturing nutrients and/or dissolved gas.

21. A method as claimed in claim 20, wherein the dissolved gases consist of one or more of oxygen, nitrogen and carbon dioxide.

22. A method as claimed in claim 20, wherein the immiscible carrier fluid is periodically purged of gases detrimental to the culturing of the cells.

23. A method as claimed in claim 19, wherein culturing the population of microdroplets comprises stirring or agitating the microdroplets by application of an optically-mediated electrowetting force at virtual electrowetting electrode locations where the microdroplets are held.

24. A method as claimed in claim 17, wherein the cell-containing first microdroplets are sorted by the output of measuring a state of the cells with an optical detection system.

25. A method as claimed in claim 17, wherein the step of creating the first microdroplets further comprises severing microdroplets from the biological sample by application of an electrowetting stretching force.

26. A method as claimed in claim 25, wherein the microdroplets are severed into the immiscible carrier fluid, the immiscible carrier fluid comprising a hydrocarbon or silicone oil.

27. A method as claimed in claim 17, wherein the immiscible carrier fluid is a fluorocarbon oil which has been optionally hydrated with aqueous micelles or secondary microdroplets.

28. A method as claimed in claim 17, wherein the reporter system is a reporter gene, cell-surface biomarker or a reporter molecule selective for an enzyme or antibody expressed by cells of the cell type being sought.

29. A method as claimed in claim 17, wherein the reporter system is a luminescent reporter cell which reacts selectively to the presence of an enzyme or antibody expressed by cells of the cell type being sought.

30. A method as claimed in claim 17, wherein the optical detection system is one of a brightfield microscope, a darkfield microscope, a means for detecting chemiluminescence, a means for detecting Förster resonance energy transfer or a means for detecting fluorescence.

31. A method as claimed in claim 17, wherein microdroplets are transported between locations on the device using an OEWOD structure adapted to generate a pathway of virtual electrowetting electrodes using electromagnetic radiation, and optionally provided with an anti-fouling and/or biocompatible coating.

32. A method for using the device of claim 1 to manipulate and/or determine one or more characteristics of cell types in a biological sample, the method comprising the steps of:
creating from the biological sample aqueous first microdroplets in an immiscible carrier fluid, at least some of which are believed to contain cells of a particular cell type;
moving the first microdroplets along a pathway using real or virtual electrowetting electrodes to at least one microdroplet inspection location; and
analysing the contents of each microdroplet with an optical detection system to determine one or more characteristics of a cell contained in that microdroplet, the one or more characteristics comprising at least one of: cell morphology, cell motility, or cell membrane integrity.

* * * * *